United States Patent
Wanami

(10) Patent No.: US 9,235,687 B2
(45) Date of Patent: Jan. 12, 2016

(54) APPARATUS FOR ESTIMATING BODILY INJURY LEVEL OF VEHICLE OCCUPANT

(71) Applicant: DENSO CORPORATION, Kariya, Aichi-pref. (JP)

(72) Inventor: Shingo Wanami, Kariya (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 14/150,169

(22) Filed: Jan. 8, 2014

(65) Prior Publication Data

US 2014/0195169 A1  Jul. 10, 2014

(30) Foreign Application Priority Data

Jan. 9, 2013  (JP) .................................. 2013-001722

(51) Int. Cl.
*G06F 19/00* (2011.01)
*G01P 15/00* (2006.01)

(52) U.S. Cl.
CPC .............. *G06F 19/345* (2013.01); *G01P 15/00* (2013.01); *G06F 19/3418* (2013.01)

(58) Field of Classification Search
CPC .... G06F 19/345; G06F 19/3418; G01P 15/00
See application file for complete search history.

(56) References Cited

U.S. PATENT DOCUMENTS

| 5,360,956 | A * | 11/1994 | Shitanoki .............. 200/61.45 R |
| 7,137,472 | B2 * | 11/2006 | Aoki ............... 180/274 |
| 7,284,769 | B2 * | 10/2007 | Breed ............... 280/735 |
| 2003/0176959 | A1 * | 9/2003 | Breed ............... 701/36 |
| 2004/0088095 | A1 * | 5/2004 | Eberle et al. .............. 701/45 |
| 2006/0208169 | A1 * | 9/2006 | Breed et al. .............. 250/221 |
| 2007/0096886 | A1 * | 5/2007 | Lich et al. .............. 340/436 |
| 2008/0156602 | A1 * | 7/2008 | Hiemenz et al. .......... 188/267.1 |
| 2008/0243342 | A1 * | 10/2008 | Breed ............... 701/45 |
| 2008/0306996 | A1 * | 12/2008 | McClellan et al. ....... 707/104.1 |
| 2010/0030432 | A1 * | 2/2010 | Ertz ............... 701/45 |
| 2010/0179730 | A1 * | 7/2010 | Hiemenz et al. .......... 701/45 |
| 2012/0078499 | A1 * | 3/2012 | Park ............... 701/301 |
| 2013/0261900 | A1 * | 10/2013 | Hu et al. ............... 701/45 |
| 2013/0317861 | A1 * | 11/2013 | Tofte et al. ............... 705/4 |
| 2013/0317865 | A1 * | 11/2013 | Tofte et al. ............... 705/4 |
| 2014/0195169 | A1 * | 7/2014 | Wanami ............... 702/19 |
| 2014/0326526 | A1 * | 11/2014 | Yasui et al. .............. 180/274 |
| 2014/0350797 | A1 * | 11/2014 | D'Addetta et al. .......... 701/45 |

FOREIGN PATENT DOCUMENTS

| JP | 2001-247005 | 9/2001 |
| JP | 2004-078393 | 3/2004 |
| JP | 2005-098886 | 4/2005 |
| JP | 2005-263178 | 9/2005 |
| JP | 2007-538297 | 12/2007 |

OTHER PUBLICATIONS

Office Action dated Jan. 20, 2015 in corresponding Japanese Application No. 2013-001722.

* cited by examiner

*Primary Examiner* — Mussa A Shaawat
*Assistant Examiner* — Kelly D Williams
(74) *Attorney, Agent, or Firm* — Harness, Dickey & Pierce, P.L.C.

(57) ABSTRACT

The present disclosure relates to an apparatus for estimating level of bodily injury of occupants at an accident of a vehicle. The apparatus has an occupancy detecting block which determines occupied seat. The apparatus has a deformation estimating block which estimates a deformation amount which is reduction of space around the seat. The apparatus has a bodily injury estimating block which estimates bodily injury level based on the occupied seat and estimated deformation amount.

8 Claims, 3 Drawing Sheets

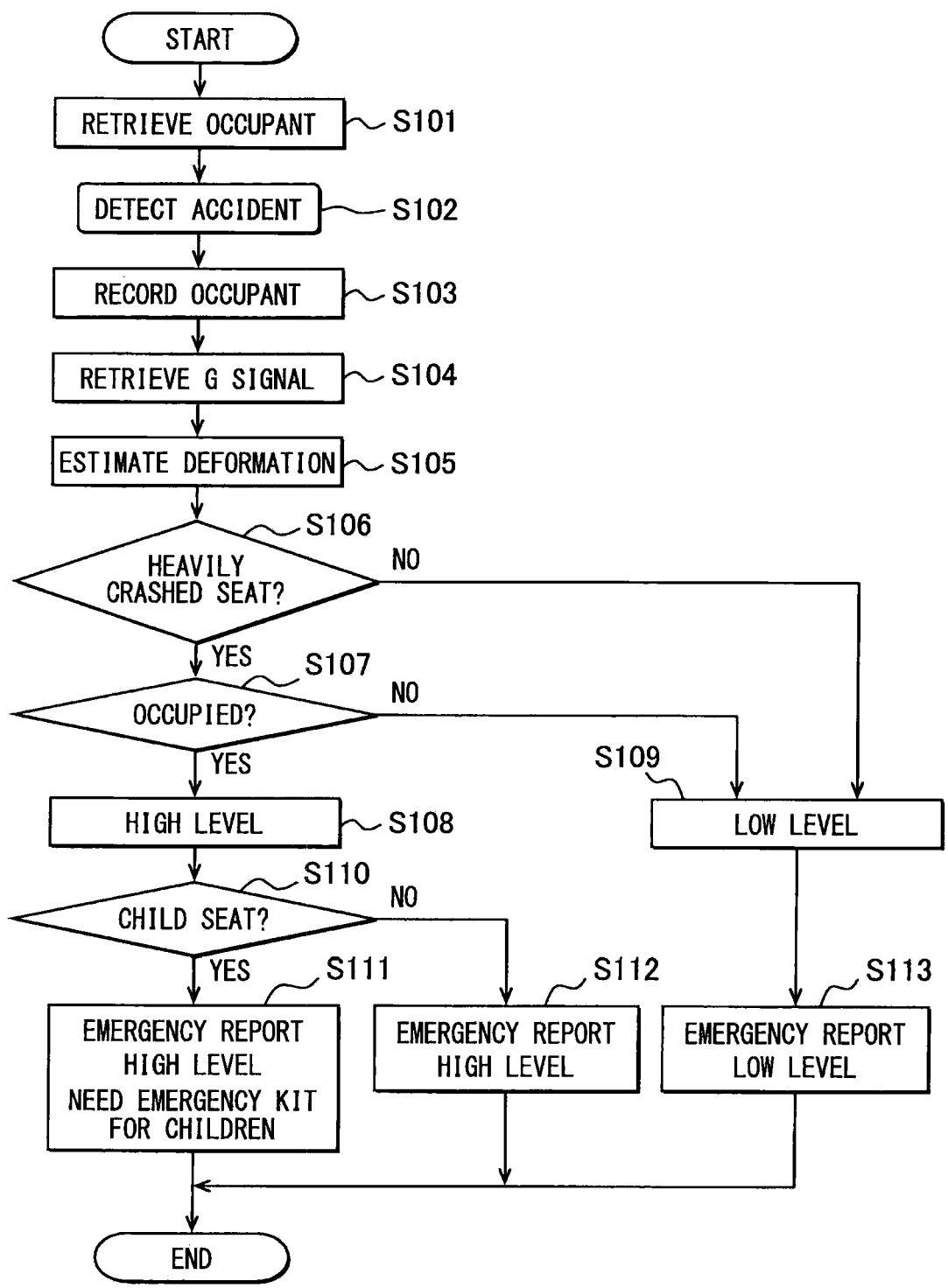

APPARATUS FOR ESTIMATING BODILY INJURY LEVEL OF VEHICLE OCCUPANT

CROSS REFERENCE TO RELATED APPLICATION

This application is based on Japanese Patent Application No. 2013-1722 filed on Jan. 9, 2013, the disclosure of which is incorporated herein by reference.

TECHNICAL FIELD

The present disclosure relates to an apparatus for estimating level of bodily injury of occupants at an accident of a vehicle.

BACKGROUND

JP2007-538297A discloses an apparatus for estimating levels of bodily injuries of vehicle occupants. This apparatus uses a sheet shaped sensor disposed on a seat, a transponder disposed in a child support seat, or a video camera which monitors inside of the vehicle. The apparatus transmits a report to a medical institution about an accident and data showing an estimated level of bodily injury of occupants.

SUMMARY

The apparatus disclosed in JP2007-538297A uses a video camera which requires devices to handle huge volume of image data. Therefore, processing loads will be increased. In addition, possibility of errors or mistakes will also be increased.

It is an object of the present disclosure to provide an apparatus which is capable of estimating bodily injury level with improved accuracy. It is an object of the present disclosure to provide an apparatus which is capable of estimating bodily injury level accurately by using simple configuration.

According to an embodiment, an apparatus for estimating level of bodily injury of occupants at an accident of a vehicle is provided. The apparatus comprises an occupancy detecting block which determines at least one of occupied seat in the vehicle. The apparatus comprises at least one acceleration sensor disposed around the seat, and a deformation estimating block which estimates deformation amount of a vehicle body based on a detection result of the acceleration sensor. The apparatus comprises a bodily injury estimating block which estimates injury level of occupants based on the result of the occupancy detecting block and the estimated result of the deformation estimating block.

According to this configuration, an occupied seat can be detected. A deformation amount of a vehicle body caused by a collision is estimated based on an acceleration sensor. Information showing the occupied seat and estimated deformation amount can show a reduced amount of an occupant space in the vehicle. This reduced amount of the occupant space allows to estimate bodily injury level of the occupant accurately. It is possible to improve accuracy of estimated bodily injury level of occupants.

BRIEF DESCRIPTION OF THE DRAWINGS

The above and other objects, features and advantages of the present disclosure will become more apparent from the following detailed description made with reference to the accompanying drawings. In the drawings:

FIG. 3 is a flow chart showing an operation of the apparatus according to the first embodiment.

DETAILED DESCRIPTION

Hereafter, embodiments of the present disclosure are explained based on the attached drawings. The drawings merely show schematic views for explanation. In the following description, a vehicle having a steering wheel on the right side is explained as an example. It may be understood that the same idea can be applied to a vehicle having a steering wheel on the left side in an opposite manner.

First Embodiment

Figure 1:
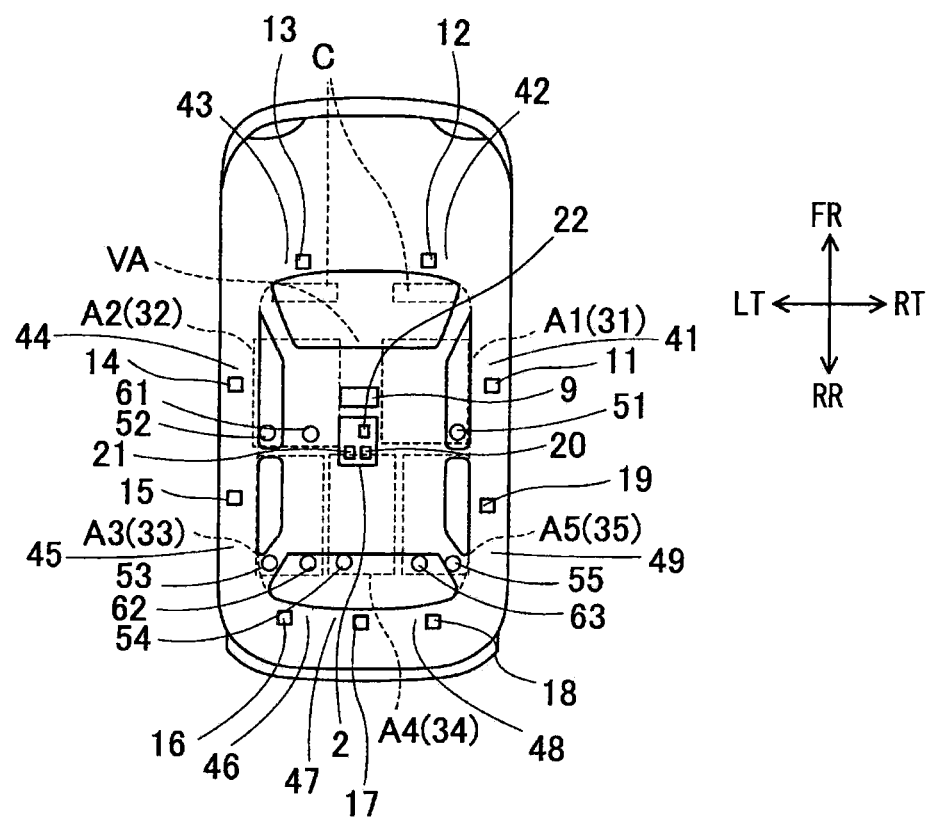
FIG. 1 is a block diagram showing an apparatus for estimating bodily injury level according to a first embodiment.

Referring to FIG. 1, the vehicle occupant bodily injury level estimating apparatus (VIEA) has acceleration sensors (GSR) 11-19, a controller for an air-bag (ECU) 2, and a wireless communication device (COM) 9. In the drawing, a front-rear direction FR-RR and a right-left direction RT-LT are indicated. An up-down direction corresponds to a vertical direction to the surface of the drawing. Each GSR 11-19 is a G-sensor. GSR 11-19 are disposed on corresponding locations on the vehicle. Each GSR 11-19 is disposed close to corresponding one of seats 31-35. For example, GSR may be disposed on a location around the corresponding seat. In this embodiment, the seats 31-35 are arranged to provide two front seats, a driver seat 31 and a passenger seat 32, and three rear seats a left seat 33, a center seat 34, and a right seat 35. Occupant restraint device, such as a seat belt 51-55 are disposed on corresponding one of the seats 31-35.

GSR 11 detects acceleration in the right-left direction, i.e., Y direction. GSR 11 is disposed on a side portion 41 on a right side of the driver seat 31. For example, GSR 11 may be disposed in a door member or a pillar member of the vehicle. GSR 11 is arranged within the side portion 41 which is disposed around the driver seat 31 to define an occupant space A1 for the driver seat 31. In other words, the side portion 41 is a member disposed directly next to the driver seat 31. GSR 12 detects acceleration in the front-rear direction, i.e., X direction. GSR 12 is disposed on a front portion 42 on a front side of the driver seat 31. For example, GSR 12 may be disposed in a dashboard or a front hood of the vehicle. GSR 12 is arranged within the front portion 42 which is disposed around the driver seat 31 to define the occupant space A1 for the driver seat 31. In other words, the front portion 42 is a member disposed directly next to the driver seat 31.

GSR 13 detects acceleration in the front-rear direction, i.e., X direction. GSR 13 is disposed on a front portion 43 on a front side of the passenger seat 32. For example, GSR 13 may be disposed in a dashboard or a front hood of the vehicle. GSR 13 is arranged within the front portion 43 which is disposed around the passenger seat 32 to define an occupant space A2 for the passenger seat 32. In other words, the front portion 43 is a member disposed directly next to the passenger seat 32. GSR 14 detects acceleration in the right-left direction, i.e., Y direction. GSR 14 is disposed on a side portion 44 on a left side of the passenger seat 32. For example, GSR 14 may be disposed in a door member or a pillar member of the vehicle. GSR 14 is arranged within the side portion 44 which is disposed around the passenger seat 32 to define the occupant space A2 for the passenger seat 32. In other words, the side portion 44 is a member disposed directly next to the passenger seat 32.

GSR 15 detects acceleration in the right-left direction, i.e., Y direction. GSR 15 is disposed on a side portion 45 on a left side of the left seat 33. For example, GSR 15 may be disposed in a door member or a pillar member of the vehicle. GSR 15 is arranged within the side portion 45 which is disposed around the left seat 33 to define an occupant space A3 for the left seat 33. In other words, the side portion 45 is a member disposed directly next to the left seat 33. GSR 16 detects acceleration in the front-rear direction, i.e., X direction. GSR 16 is disposed on a rear portion 46 on a rear side of the left seat 33. For example, GSR 16 may be disposed in a trunk of the vehicle. GSR 16 is arranged within the rear portion 46 which is disposed around the left seat 33 to define the occupant space A3 for the left seat 33. In other words, the rear portion 46 is a member disposed directly next to the left seat 32.

GSR 17 detects acceleration in the front-rear direction, i.e., X direction. GSR 17 is disposed on a rear portion 47 on a rear side of the center seat 34. For example, GSR 17 may be disposed in the trunk of the vehicle. GSR 17 is arranged within the rear portion 47 which is disposed around the center seat 34 to define an occupant space A4 for the center seat 34. In other words, the rear portion 47 is a member disposed directly next to the center seat 34.

GSR 18 detects acceleration in the front-rear direction, i.e., X direction. GSR 18 is disposed on a rear portion 48 on a rear side of the right seat 35. For example, GSR 18 may be disposed in the trunk of the vehicle. GSR 18 is arranged within the rear portion 48 which is disposed around the right seat 35 to define an occupant space A5 for the right seat 35. In other words, the rear portion 48 is a member disposed directly next to the right seat 35. GSR 19 detects acceleration in the right-left direction, i.e., Y direction. GSR 19 is disposed on a side portion 49 on a right side of the right seat 35. For example, GSR 19 may be disposed in a door member or a pillar member of the vehicle. GSR 19 is arranged within the side portion 49 which is disposed around the right seat 35 to define the occupant space A5 for the right seat 35. In other words, the side portion 48 is a member disposed directly next to the right seat 35. At least one of GSR 11-19 is disposed in one of the portions 41-49 which defines one of the occupant spaces A1-A5 provided for corresponding one of the seats 31-35. As a result, GSR 11-19 are disposed between the occupant space A1-A5 and a colliding object such as an incoming object.

GSR 11-19 are connected to ECU 2 to enable data communication. A room VA is defined by the portions 41-49, and includes the occupant spaces A1-A5. GSR 11-19 are disposed on an outside of the room VA.

The ECU 2 is an electronic control unit which controls deployment of an air-bag which is an occupant protection device. The ECU 2 is arranged on a center of the vehicle. Although ECU 2 is used to provide the estimating apparatus, other ECU in the vehicle or device linked by data network may be used to provide the estimating apparatus.

ECU 2 is arranged in a non-exposed portion, for example, in an accommodation box, in the room VA of the vehicle. ECU 2 is mainly provided with a microcomputer 20, an auxiliary acceleration sensor (ASR) 21, and an event recorder (REC) 22. REC 22 provides and corresponds to an accident recorder. The event recorder 22 records information relating to accidents. The auxiliary acceleration sensor 21 is disposed on a center of the vehicle. ASR 21 is a sensor which measures three dimensional accelerations in the front and rear direction (X axis direction), the right and left direction (Y axis direction), and an up and down direction (Z axis direction).

Figure 2:
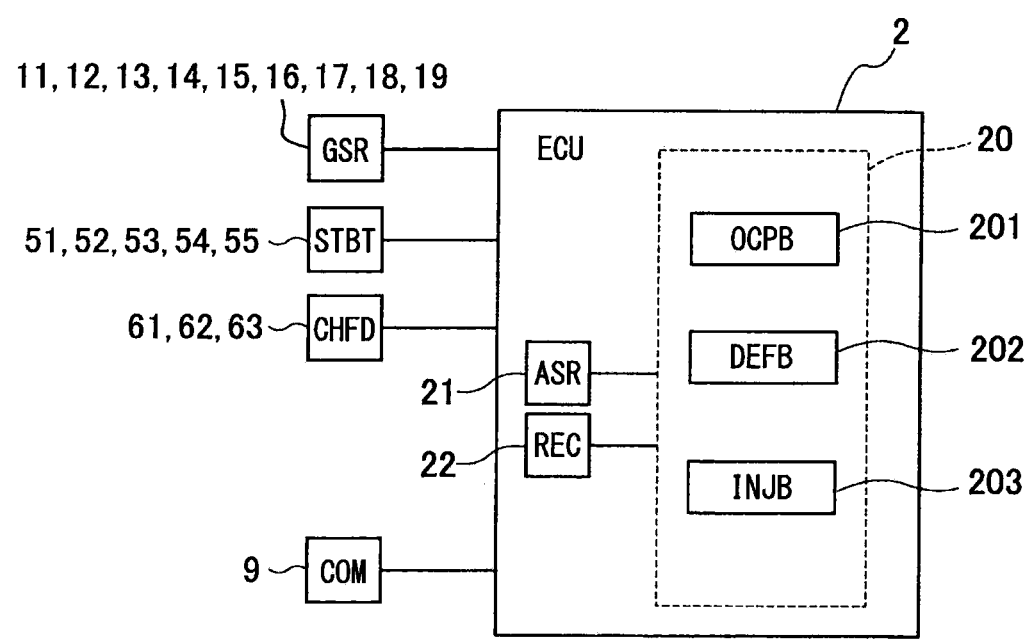
FIG. 2 is a block diagram showing details of the apparatus according to the first embodiment.

As shown in FIG. 2, ECU 2 provides functional blocks mainly realized by the microcomputer 20. ECU 2 provides an occupancy detecting block (OCPB) 201. ECU 2 provides a deformation estimating block (DEFB) 202. ECU 2 provides a bodily injury estimating block (MB) 203.

The control unit (controller) is an electrical control unit (ECU). The controller has at least one processing unit (CPU) and at least one memory device (MMR) provided as a storage medium which stores a set of program and data. The controller is provided with a microcomputer having the storage medium readable by a computer. The storage medium is a non-transitory storage medium which stores a program readable by the computer. The storage medium can be provided by a device, such as a solid state memory device and a magnetic disc memory. The controller is provided with one computer, or a set of computer resources linked by a data communication device. The program, when executed by the controller, makes the controller to function as devices described in this specification, and makes the controller to perform methods described in this specification. The controller provides a plurality of various elements. At least a part of those elements may be called as means for performing functions, and, in another aspect, at least a part of those elements may be called as structural blocks or modules.

OCPB 201 determines whether an occupant exist on corresponding seat or not. OCPB 201 detects an occupant by detecting use of corresponding one of seat belts (STBT) 51-55, which are disposed on the seats 31-35, respectively. OCPB 201 determines at least one of occupied seat 51-55 in the vehicle. OCPB 201 detects whether corresponding one of seat belts 51-55 disposed on the seats 31-35 is used or not. OCPB 201 receives signals from the seat belts 51-55. For example, the seat belts 51-55 output signal when a male buckle is inserted and locked with a female buckle. Therefore, OCPB 201 can determine whether an occupant on the specific seat 31-35 or not based on the signal from the seat belts 51-55. For this purpose, each one of the seat belts 51-55 may have a switch to output signal when the male buckle is inserted and locked with the female buckle. OCPB 201 can detect state of the seat belts 51-55 by monitoring the signals. ECU 2 is connected with the seat belts 51-55 to perform data communication. ECU 2 receives signals from the seat belts 51-55 and at least detects use of the seat belts 51-55.

In addition, child restraint seat fixing devices (CHFD) 61-63 are disposed on corresponding one of the seats 32-35. CHFD 61-63 may be provided by standard devices defined as ISO-FIX type. The child restraint seat (CRS) includes an infant seat and a booster seat. OCPB 201 detects whether which seat 32, 33, 35 is installed with CRS by receiving signal, which is outputted when a connector of CRS is connected and locked with a fixing receiver 61-63. Each one of the fixing receiver 61-63 has a switch, respectively, which is turned on when CRS is properly installed. The switch transmits signal to ECU 2. That is, OCPB 201 detects whether CRS is installed in corresponding one of the seats 31-35 or not.

Thus, OCPB 201 detects and determines seats on which occupants exist by detecting and determining whether the seat belt 51-55 is used or not, and whether CRS is used or not. OCPB 201 or INJB 203 determines that "occupant exists" on the specific one of the seats 31-35, when it receives at least one of signals which shows turning on of the switches for the seat belts 51-55 and turning on of the switches for CRS. In other words, the seat belts 51-55 and the fixing receiver 61-63 are components for detecting occupancy on the seats 31-35. OCPB 201, the seat belts 51-55 and the fixing receiver 61-63 provides means for detecting occupancy on the seats 31-35.

DEFB 202 estimates deformation amount of a vehicle body based on at least one of the detection result of GSR 11-19, and the detection result of ASR 21. In detail, DEFB 202 determines that "there is a collision", when at least one of the detection results of GSR 11-19 or ASR 21 exceeds corresponding one of predetermined thresholds, i.e., collision thresholds. DEFB 202 calculates a double integral of the detection result, i.e., acceleration, of GSR 11-19 in order to calculate a first deformation b1. In addition, when DEFB 202 determines a collision, DEFB 202 also calculates double integrals of detection results in the X direction and the X direction of ASR 21 respectively in order to calculate a second deformation b2. Then, DEFB 202 calculates a deformation amount caused by a collision by subtracting the second deformation b2 from the first deformation b1 (b1-b2) after adjusting directions, e.g., after converting components of the deformations in the colliding direction.

For example, a deformation amount is calculated by subtracting the second deformation based on the detection result, which shows acceleration in the Y direction, of ASR 21, from the first deformation based on the detection result of GSR 11, which detects acceleration in the Y direction. A decreased amount of space for the occupant space A1 can be calculated based on a deformation amount detected by GSR 11 and a deformation amount detected by GSR 12. That is, a decreased amount of space for the occupant space A1 is calculated based on the detection results from the acceleration sensors 11, 12, and 21. A decreased amount of space for the occupant space A2 is calculated based on the detection results from the acceleration sensors 13, 14, and 21. A decreased amount of space for the occupant space A3 is calculated based on the detection results from the acceleration sensors 15, 16, and 21. A decreased amount of space for the occupant space A4 is calculated based on the detection results from the acceleration sensors 17 and 21. A decreased amount of space for the occupant space A5 is calculated based on the detection results from the acceleration sensors 18, 19, and 21. That is, DEFB 202 estimates the decreased amount based on the detection results of both GSR 11-19 and ASR 21.

DEFB 202 may employ other calculating methods which can estimate an amount of space reduced by a crash. For example, DEFB 202 may calculate a reduced amount of space by calculating a double integral after calculating a difference between the first deformation and the second deformation. DEFB 202 may calculate a reduced space by using a data base, i.e., a map, in which a reduced space may be estimated by looking up the map based on the first deformation and the second deformation.

DEFB 202 estimates deformation amount of a vehicle body close to the seats 31-35 by calculating deformation amount caused by a crash based on the detection result of the acceleration sensors, such as at least one of GSR or ASR. That is, DEFB 202 estimates deformation of a vehicle body. DEFB 202 sends estimated result to INJB 203.

INJB 203 estimates injury level of occupants based on the result of OCPB 201 and the estimated result of DEFB 202. INJB 203 estimates and determines bodily injury level of an occupant on a seat based on the estimated result from DEFB 202 and the detected result from OCPB 201. INJB 203 estimates bodily injury level based on a deformation amount of the vehicle body around a seat where an occupant exists. In other words, INJB 203 estimates bodily injury level based on a reduced amount of an occupant space around a seat where an occupant exists. In order to determine a deformation amount of the vehicle body and/or a reduced amount of an occupant space, INJB 203 combines the estimated result from DEFB 202 and the detected result from OCPB 201. INJB 203 compares the seat positions or the occupant spaces A1-A5 indicated by the estimated result, i.e., a deformation amount of the vehicle body or a reduced amount of the occupant space A1-A5, and the seat positions where OCPB 201 detects an occupant.

INJB 203 increases bodily injury level to rise seriousness as a deformation amount of the vehicle body on the seat where an occupant exists increases. INJB 203 estimates and sets a high level for bodily injury level when the amount of deformation or the amount of space reduction exceeds a predetermined emergency threshold. INJB 203 estimates and sets a low level for bodily injury level when the amount of deformation or the amount of space reduction does not exceed a predetermined emergency threshold, e.g., the amount is sufficiently low or 0 (zero). INJB 203 estimates and sets a high level for bodily injury level of a child when the amount of deformation or the amount of space reduction at a seat where CRS is mounted is large, e.g., exceeds a predetermined emergency threshold. INJB 203 may estimate and determine bodily injury level by first confirming a seat position where an occupant exists, and then, referencing the amount of space reduction at the confirmed seat position. INJB 203 may estimate and determine bodily injury level by first calculating amounts of space reduction at each seat, and then, confirming a seat position where an occupant exists. The bodily injury level, which is estimated by INJB 203, can be used as an index indicative of degree of occupant's injury or emergency level of injury.

INJB 203 controls REC 22 to record accident information, which may contain the estimated result, such as an estimated deformation amount and an estimated bodily injury level, and information from the other ECU. INJB 203 also controls COM 9 by sending an instruction signal to make a report to the predetermined entity. REC 22 is a data recorder, such as a nonvolatile memory device, which records data showing the estimated result of INJB 203 and data showing condition of the vehicle at an accident. The estimated result to be recorded may contain a seat position where an occupant exists, a deformed position, and an amount of deformation. The condition at an accident may contain a vehicle speed, brake instructions, location information provided by GPS, etc.

COM 9 is a device which makes possible telephone call and data communication by wireless transmitter and receiver. COM 9 may be provided by a wireless communication ECU on the vehicle which performs as a terminal device of a telecommunication system. COM 9 automatically reports accident information including the estimated result of bodily injury level to a predetermined entity when the bodily injury estimating block estimates bodily injury level. An example of the predetermined entity is an organization which may operate emergency service or has power to order emergency service directly or indirectly. For example, the predetermined entity may be a public organization, such as a public emergency call center for fire authorities or police stations etc. The predetermined entity may be a private organization, such as an emergency hospital, an emergency hospital operating a doctor helicopter, a company operating ambulances, or a vehicle related service company which usually established by a vehicle maker and may be called as a vehicle management center, an operation center or an operation service company.

An example of operation of the apparatus, which is mainly operation of ECU 2, for estimating injury level of occupants is explained. FIG. 3 shows processing for estimating level of injury. Steps are referenced by numbers with "S". In S101, ECU 2 retrieves information showing occupied seat. In other words, it is determined that locations of a seat on which a passenger exists. For example, at least one of the seats 51-55 is detected as an occupied seat. In S102, an accident of collision is detected based on signals from ASR 21 or at least one of GSR 11-19. In S102, ECU 2 records the accident and information showing locations of the occupied seats at the accident in the event recorder 22. In other words, occupancy condition of the seats is recorded. In S104, the detection results at a collision are transmitted to DEFB 202 from GSR 11-19 and ASR 21. In S105, reduced amounts of each one of the occupant spaces A1-A5 are calculated by calculating deformation amounts of the vehicle body on corresponding position where GSR 11-19 are disposed. That is, DEFB 202 calculates double integrals for each one of GSR 11-19 and consolidates the double integrals to estimate reduced amounts of each one of the occupant spaces A1-A5.

In S106, it is determined that whether there is at least one of the occupant spaces A1-A5 where an amount of space reduction exceeds the emergency threshold or not. In other words, in S106, INJB 203 determines that whether there is a heavily crashed seat. This process is performed by. In a case that there is at least one of the occupant spaces A1-A5 where an amount of space reduction exceeds the emergency threshold, the process branches to YES from S106 and proceeds to S107. The occupant space where an amount of space reduction exceeds the emergency threshold may be called as a crashed occupant space. In S107, it is determined that whether an occupant exists on a seat corresponding to the crashed occupant space based on the detection result of OCPB 201. In a case that an occupant exists on a seat corresponding to the crashed occupant space, the process branches to YES from S107 and proceeds to S108. In S108, it is determined that a high level is estimated.

In a case that an estimated level is the high level, in S110, it is determined that whether CRS is used as a restraint device for an occupant or not based on the detection result from OCPB 201. In a case that CRS is used, the process branches to YES from S110 and proceeds to S111. In S111, it is determined that there is at least one child who may be injured with a high level, i.e., who may be seriously injured. In S111, COM 9 sends a report to the predetermined entity. The report contains information about the estimated bodily injury level. The report contains information showing an occupant may be a child. For this purpose, the report may contain information showing advice for emergency workers, such as an emergency kit or equipment for children may be needed. The report contains information about an accident. INJB 203 estimates and sets emergency level to a high level when bodily injury level is estimated a high level. In a case that CRS is not used, the process branches to NO from S110 and proceeds to S112. In S112, it is determined that at least one occupant may be injured with a high level. In S112, COM 9 sends a report to the predetermined entity. The report contains information about the estimated bodily injury level. The report contains information showing an occupant may not be a child. For this purpose, the report may contain information showing advice for emergency workers, such as an emergency kit or equipment for children may not be needed. The report contains information about an accident.

In a case that there is no occupant space of which reduced amount of space exceeds the emergency threshold, the process branches to NO from S106 and proceeds to S109. In a case that there is no occupant in the occupant space of which reduced amount of space exceeds the emergency threshold, the process branches to NO from S107 and also proceeds to S109. In S109, it is determined that bodily injury level is a low level. If bodily injury level is determined, in S113, COM 9 sends a report containing information about bodily injury level and accident to the predetermined entity. INJB 203 estimates and sets emergency level to a low level when bodily injury level is estimated a low level. The process may be modified to switch performing a report or not according to emergency level. For example, INJB 203 may instruct a report only when the emergency level is set at a high level. In this embodiment, bodily injury level and emergency level are categorized into two levels, high or low. Alternatively, those level may be divided and classified in still more steps finely to increase levels.

According to the embodiment, in a case of a collision, a deformation amount of a vehicle body caused by the collision can be estimated based on at least one of acceleration sensors 11-19 and 21. An occupied seat can be determined. Information showing the occupied seat and estimated deformation amount can provide sufficient data to estimate a reduced amount of an occupant space in the vehicle. This reduced amount of the occupant space allows to estimate bodily injury level of occupants accurately. According to the embodiment, it is possible to improve accuracy of estimating bodily injury level of occupants. In this embodiment, it is possible to estimate bodily injury level with sufficient accuracy by using simple configuration. For example, in this embodiment, bodily injury level can be accurately estimated without using devices, such as a video camera and a processor for video data. It is possible to estimate bodily injury level by using a simple configuration using acceleration sensors. It is possible to reduce errors and mistakes in calculations, and to estimate bodily injury level with sufficient accuracy. It is also possible to reduce cost of the apparatus. In this embodiment, GSR 11-19 may be provided by satellite G sensors, which are usually used in an occupant restraint system such as an airbag system. In addition, ASR 21 may be provided by an acceleration sensor on ECU 2 for the occupant restraint system. Therefore, it is also possible to provide the apparatus in low cost.

In this embodiment, in a case that a bodily injury level is determined, information including the estimated result of bodily injury level is automatically reported to a predetermined entity via COM 9. Thereby, it is possible to facilitate subsequent rescue works. In addition, since the information about there is CRS or not, i.e., the occupants include at least one child or not, is also reported to the entity, it is possible to facilitate more appropriate rescue works.

Occupancy on each seat is determined based on information indicative of use of the seat belts 51-55 and use of CRS mounting devices. It is possible to detect and determine position of occupants at a collision accurately. It is also possible to determine that occupants are restrained on the seats 31-35. Since the embodiment estimates bodily injury level based on deformation amount of vehicle body, it is assumed that a bodily injury level of an occupant is closely related to a reduced amount of space for the corresponding occupant. Therefore, estimated bodily injury level can have sufficient reliability.

Since GSR 11-19 are provided on vehicle body members that define the occupant spaces A1-A5, it is possible to calculate reduced amount of spaces directly. That is, it is possible to estimate deformation of a vehicle body accurately, and to estimate bodily injury level accurately. The GSR 11-19 may be disposed on the other members of the vehicle body which defines the room VA.

Deformation of a vehicle body is estimated by using the detection result of ASR 21 which detects accelerations on entire vehicle body, i.e., accelerations including accelerations caused by movement of the vehicle body. Thereby, it is possible to extract accelerations relating to deformation of the vehicle body by removing components of accelerations caused by movement of the vehicle body from the detection results of GSR 11-19. Since deformation of the vehicle body is calculated based on the accelerations only related to deformation of the vehicle body, it is possible to estimate deformation amount of the vehicle body with sufficient accuracy.

Other Embodiments

The present disclosure is not restricted to preceding embodiments. For example, DEFB 202 may calculate modification of a vehicle body based on the detection result of GSR 11-19 without using the detection result of ASR 21. For example, DEFB 202 may calculate a deformation, i.e., an amount of space reduction, of a vehicle body by calculating a double integral of the detection result of GSR 11-19. In this modification, it is possible to simplify an estimating process of injury level. However, the preceding embodiments are more advantageous in estimating accuracy.

OCPB 201 may use other occupant detecting sensors mounted on the seats 31-35, such as a capacitive type, pressure type, or load-detecting type, instead of the switches on the seat belts. The existence of CRS may be detected by a wireless communication between CRS and a seat.

Moreover, deformation estimating process may be performed based on only GSR 11-19 of which detection results exceed the thresholds. Deformation estimating process may be performed based on only GSR 11-19 disposed around at least one of the occupant spaces A1-A5 around which at least one of GSR 11-19 of which detection results exceed the thresholds is disposed. In those cases, level of bodily injury is also determined based on the results of whether a seat position where deformation is estimated and a seat position where an occupant is detected are the same or not, and of whether the deformation caused by a crash exceeds the emergency threshold or not. Moreover, calculating formula may incorporate weight or coefficient, which is indicative of ability of deformation of vehicle body portions where GSR 11-19 are disposed, such as side members, a front member, and a rear member, in order to improve accuracy.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, are preferred, other combinations and configurations, including more, less or only a single element, are also within the spirit and scope of the present disclosure.

What is claimed is:

1. An apparatus for estimating a level of bodily injury of occupants at an accident of a vehicle, comprising:
an occupancy detecting block which determines at least one occupied seat from a plurality of seats in the vehicle;
a plurality of acceleration sensors, at least one acceleration sensor disposed on portions around each of the plurality of seats, respectively, the portions defining occupant spaces corresponding to the plurality of seats, respectively, the plurality of acceleration sensors including a plurality of occupied seat acceleration sensors, at least one occupied seat acceleration sensor disposed on portions around each of the occupied seats and a plurality of non-occupied seat acceleration sensors, at least one non-occupied seat acceleration sensor disposed on portions around each of the non-occupied seats;
a deformation estimating block which estimates a deformation amount of a vehicle body corresponding to the occupant space of the occupied seats based on a detection result of the occupied seat acceleration sensors; and
a bodily injury estimating block which estimates the level of bodily injury of occupants based on the result of the occupancy detecting block and the estimated result of the deformation estimating block; wherein
the plurality of seats includes a first seat and a second seat, and wherein
the plurality of acceleration sensors comprises:
a first group of acceleration sensors disposed around the occupant space of the first seat, the first group of acceleration sensors including a first acceleration sensor and a common acceleration sensor; and
a second group of acceleration sensors disposed around the occupant space of the second seat, the second group of acceleration sensors including a second acceleration sensor and the common acceleration sensor, and wherein
the deformation estimating block, when the first seat is the occupied seat, estimates the deformation amount of the vehicle body corresponding to the occupant space of the first seat based on the detection result of the first group of acceleration sensors, and when the second seat is the occupied seat, estimates the deformation amount of the vehicle body corresponding to the occupant space of the second seat based on the detection result of the second group of acceleration sensors;
the first seat is a driver seat, and the second seat is a passenger seat, and wherein
the first group of acceleration sensors includes:
a driver side acceleration sensor disposed on a member directly next to the driver seat; and
a driver front acceleration sensor disposed on a front side of the driver seat, wherein one of the driver side acceleration sensor or the driver front acceleration sensor is the first acceleration sensor, and wherein
the second group of acceleration sensors includes:
a passenger side acceleration sensor disposed on a member directly next to the passenger seat; and
a passenger front acceleration sensor disposed on a front side of the passenger seat, wherein one of the passenger side acceleration sensor or the passenger front acceleration sensor is the second acceleration sensor, and wherein
the common acceleration sensor is disposed on a center of the vehicle.

2. The apparatus for estimating level of bodily injury claimed in claim 1, further comprising:
a wireless communication device which reports accident information including the estimated result of the bodily injury level to a predetermined entity when the bodily injury estimating block estimates the bodily injury level.

3. The apparatus for estimating level of bodily injury claimed in claim 1, wherein the occupancy detecting block detects whether a corresponding one of seat belts disposed on the seats is used or not.

4. The apparatus for estimating level of bodily injury claimed in claim 1, wherein the occupancy detecting block detects whether a child restraint seat is installed in a corresponding one of the seats or not.

5. The apparatus for estimating level of body injury claimed in claim 1, wherein the deformation estimating block estimates a reduced amount of the occupant space.

6. The apparatus for estimating level of body injury claimed in claim 1, wherein the deformation estimating block estimates reduced amounts of the occupant spaces, and wherein the deformation estimating block determines whether there is at least one of the occupant spaces where the reduced amount exceeds an emergency threshold or not.

7. The apparatus for estimating level of body injury claimed in claim 6, wherein the deformation estimating block estimates the reduced amount of the occupant space by calculating a double integral of the detection result of the acceleration sensors.

8. The apparatus for estimating level of bodily injury claimed in claim 1, wherein
the deformation estimating block, in estimating the deformation amount of the vehicle body corresponding to the occupant space of the occupied seat, only uses the detection result of the occupied seat acceleration sensors, and doesn't use the detection result of the non-occupied seat acceleration sensors.

* * * * *